US00PP18217P2

(12) United States Plant Patent
Sanders

(10) Patent No.: US PP18,217 P2
(45) Date of Patent: Nov. 13, 2007

(54) ***IMPATIENS* PLANT NAMED 'IMTRARESTAR'**

(50) Latin Name: *Impatiens walleriana*
Varietal Denomination: Imtrarestar

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/438,417

(22) Filed: May 22, 2006

(51) Int. Cl.
*A01H 5/00* (2006.01)

(52) U.S. Cl. ..... Plt./317
(58) Field of Classification Search ..... Plt./317
See application file for complete search history.

(56) References Cited

U.S. PATENT DOCUMENTS

PP17,238 P3 * 11/2006 Sanders ..... Plt./317

OTHER PUBLICATIONS

UPOV ROM GTITM Computer Database, GTI Jouve Retrieval Software 2006/04 Citations for 'Imtrarestar'.*

* cited by examiner

*Primary Examiner*—Wendy C Haas
(74) *Attorney, Agent, or Firm*—Bruce Vrana

(57) ABSTRACT

A new *Impatiens* plant, characterized particularly as to novelty by a flat and strong outward spreading growth habit, freely branching with branches that tend to grow horizontally, resulting in a big and floriferous plant with large carmine flowers with a distinct white star pattern.

1 Drawing Sheet

Latin name of the genus and species of the plant claimed: *Impatiens walleriana.*
Varietal denomination: 'Imtrarestar'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar has a flat and spreading growing type, is floriferous with large flowers with a distinct star pattern and has attractive dark foliage.

The present cultivar originated from a cross-pollination made in 2002, of a proprietary *Impatiens* selection identified as 'T3108-2,' not patented, as the female, or seed parent, with a proprietary *Impatiens* selection identified as 'T2463-1,' not patented, as the male, or pollen parent.

The present cultivar has been repeatedly asexually reproduced by cuttings in Enkhuizen, Netherlands, in Angers, France, in Gilroy, USA over a two year period. The distinctive characters of this new *Impatiens* are stable and reproduced true to type in successive generations of asexual reproduction. It takes 6 to 8 weeks to produce a finished plant, depending on the temperature.

This new *Impatiens* plant is an annual in most climatical zones in the US, only in zones 9 and 10 its a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Impatiens.* The data which defines these characteristics were collected from asexual reproductions carried out in Enkhuizen, Netherlands. The plant history was taken on 20 week old plants, blossomed under natural light in the field.

Color readings were taken in the office under ambient light. Color references are primarily to The R.H.S. Color Chart of The Royal Horticultural Society of London.

Plants of the new *Impatiens* differ primarily from the plants of the female parent selection in the followig characteristics:

Plants of the new *Impatiens* have large, carmine flowers with a distinct star pattern and a trailing habit, whereas the plants of the female have medium sized purple flowers with a slight star pattern.

Plants of the new *Impatiens* differ primarily from the male plant selection in the following characteristics:

Plants of the new *Impatiens* have a trailing plant habit and a carmine flower with a white star pattern, whereas the plants of the male have a compact, upright plant habit and a red flower with a white star pattern.

TABLE 1

DIFFERENCES BETWEEN THE NEW CULTIVAR 'IMTRARESTAR' AND A SIMILAR CULTIVAR

| | 'Imtrarestar' | 'Imtrarose' (U.S. Plant Patent No. 17,238) |
|---|---|---|
| Flower color | Carmine with white star | Rose |
| Flowersize | Large | Large |
| Number of flowers | Fairly floriferous | Floriferous |
| Habit | Medium long trailing branches | Long trailing branches |

The family relationship between 'Imtrarestar' and 'Imtrarose' is: The female parent line of 'Imtrarestar' is a cross of 'T0404-1' with line 'R2938.' 'R2938' is ('RBGE 19821569'×'J475-2' crossed with 'M1007-1') crossed with ('RBGE 19821569'×'G2171-1' crossed with 'RBGE 19821569'×'J475-2'). The male parent line of 'Imtrarose' is 'RBGE 19821569'×'J475-2' crossed with 'M1007-1.'

Parentage:
*Female parent.*—'T3108-2,' not patented.
*Male parent.*—'T2463-1,' not patented.
Propagation:
*Type cutting.*—Terminal cuttings.
*Time to initiate roots.*—10–12 days at 20 degrees C.
*Time to produce a rooted cutting.*—4 weeks.
*Root description.*—Fine, fibrous and white in color.
Plant description:
*General appearance.*—Makes long branches that tend to grow horizontally.
*Habit.*—Flat and spreading growing type.
*Growth and branching habit.*—Freely branching habit, freely flowering, vigorous.
*Crop time.*—7–9 weeks from unrooted cutting in a 12 cm pot.
*Plant height.*—26 cm.
*Plant spread.*—70 cm.
Lateral branch description:
*Length.*—20–30 cm.
*Diameter.*—8 mm.
*Texture.*—Smooth, glabrous.
*Internode length.*—1–6 cm.
*Color.*—RHS 146C with little anthocyanin RHS 64A.
Foliage description:
*Arrangement.*—Alternate.
*Length, mature leaves.*—5.5 cm.
*Width, mature leaves.*—4 cm.
*Shape.*—Ovate-cordate.
*Apex.*—Acuminate.
*Base.*—Acute.
*Margin.*—Crenate-serrate.
*Texture.*—Smooth, glabrous.
*Venation pattern.*—Pinnate.
*Color young foliage, upper surface.*—RHS 139A.
*Color young foliage, lower surface.*—139C with anthocyanin spots RHS 64A.
*Fully expanded foliage, upper surface.*—RHS 139A.
*Fully expanded foliage, lower surface.*—RHS 148B.
*Venation, upper surface.*—RHS 139A, Anthocyanin is present.
*Venation, lower surface.*—RHS 199A, Anthocyanin is present.
*Petiole, length.*—About 3.5 cm.
*Petiole, diameter.*—About 2 mm.
*Texture.*—Smooth, glabrous.
*Color.*—RHS 199C.
Flower description:
*Flower type and flowering habit.*—Single.
*Number of flowers per leaf axil.*—3.
*Number of flowers and flower buds per lateral branch.*—25.
*Flower position.*—Above and beyond the foliage and typically facing upwards and outward.
*Flower shape.*—Rounded, mostly flat. Flowers lasting about 7–9 days on the plant depending on environmental conditions Flowers non persistent Flowers not fragrant Flowering indeterminate and continuous.
*Flowering season.*—Year round under greenhouse conditions. In the garden, flowering from spring until fall.
*Flower diameter.*—About 4.5 cm.
Flower buds:
*Rate of opening.*—From flower bud to fully open flower, typically about 6–8 days depending on temperature.
*Bud length (at stage of showing color).*—About 1.3 cm.
*Bud diameter.*—About 1 cm.
*Bud shape.*—Ovoid.
*Texture.*—Smooth, glabrous.
*Color, just before opening.*—RHS 155B and RHS 54B.
Petals:
*Quantity.*—Single, five per flower, imbricate.
*Length of banner petal.*—About 1.9 cm.
*Width of banner petal.*—About 2.3 cm.
*Length lateral and basal petals.*—About 2.3 cm.
*Width lateral and basal petals.*—About 1.8 cm.
*Lateral and basal petal shape.*—Obovate-spathulate.
*Banner petal shape.*—Broadly obcordate.
*Petal apex.*—Retuse to emarginate.
*Petal base.*—Rounded, attenuate.
*Petal margin.*—Entire.
*Petal texture.*—Smooth, satiny.
*Petal color.*—Upper surface when opening and fully opened: RHS 155B in the middle of the petals and sides of the petals are RHS N66A to RHS N66B towards the middle stripe. Lower surface when opening and fully opened: RHS 155B in the middle of the petal and the sides of the petal are RHS 52B.
Sepals:
*Lateral sepals.*—2.
*Shape.*—Ovate-lanceolate.
*Apex.*—Acute.
*Margin.*—Entire.
*Length.*—3–7 mm.
*Texture upper and lower surface.*—Smooth, glabrous.
Spur:
*Length.*—About 3.5 cm.
*Texture.*—Smooth, glabrous.
*Aspect.*—Curved.
*Color.*—RHS 51D at the broad part and yellow-green to the end RHS 145B.
Peduncles:
*Length.*—About 1.5 cm.
*Diameter.*—1 mm.
*Aspect.*—About 45 degrees from the stem.
*Color.*—RHS 167A.
*Bracts.*—At least 2.
*Shape.*—Linear-lanceolate.
*Apex.*—Acute.
*Length.*—3–6 mm.
*Color.*—RHS 146B.
Reproductive organs:
*Androecium.*—Stamen number: Five fused at anthers, filaments free, hooded. Anther shape: Obovate. Anther length: About 4 mm. Anther colour: RHS 156A with RHS 58D. Amount of pollen: No pollen.
*Gynoecium.*—Pistil number: One. Pistil length: About 5 mm. Stigma shape: Colomnar, five segmented. Stigma color: Colorless. Style color: RHS 136A. Ovary arrangement: Five celled. Ovary colour: RHS 136A.
Seed development: Seed development has not been observed.

What is claimed is:

1. A new and distinct cultivar of *Impatiens* plant named 'Imtrarestar,' as substantially illustrated and described herein.

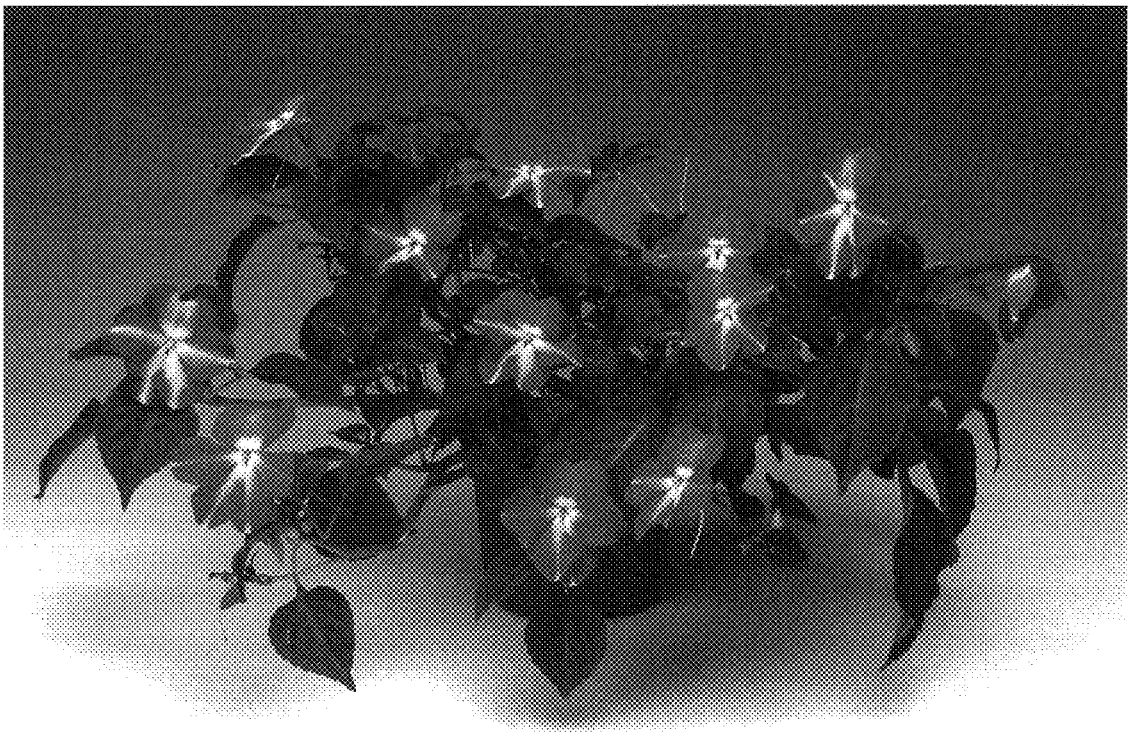

* * * * *